(12) United States Patent
Stuttard

(10) Patent No.: US 7,244,939 B2
(45) Date of Patent: Jul. 17, 2007

(54) GAS SENSOR

(75) Inventor: David Michael Stuttard, Notts (GB)

(73) Assignee: Dynament Limited, Nottingham (GB)

( * ) Notice: Subject to any disclaimer, the term of this patent is extended or adjusted under 35 U.S.C. 154(b) by 45 days.

(21) Appl. No.: 10/929,350

(22) Filed: Aug. 30, 2004

(65) Prior Publication Data

US 2005/0121614 A1 Jun. 9, 2005

(30) Foreign Application Priority Data

Dec. 9, 2003 (GB) ................................. 0328684.6
Jun. 24, 2004 (GB) ................................. 0414127.1

(51) Int. Cl.
*G01J 5/08* (2006.01)
(52) U.S. Cl. ...................... 250/343; 250/349; 250/345; 250/344; 356/437
(58) Field of Classification Search ................. 250/344, 250/345
See application file for complete search history.

(56) References Cited

U.S. PATENT DOCUMENTS

| | | | |
|---|---|---|---|
| 4,700,079 A * | 10/1987 | Ito | 250/574 |
| 5,601,693 A * | 2/1997 | Davies | 204/400 |
| 5,834,777 A | 11/1998 | Wong | |
| 6,016,203 A * | 1/2000 | Martin | 356/432 |
| 6,469,303 B1 * | 10/2002 | Sun et al. | 250/343 |
| 2002/0063216 A1 * | 5/2002 | Clausen et al. | 250/343 |

FOREIGN PATENT DOCUMENTS

| GB | 2172701 | 9/1986 |
|---|---|---|
| GB | 2372099 B | 8/2002 |
| GB | 2 392 721 | 10/2004 |

OTHER PUBLICATIONS

Ion Optics, Inc., IR-IS Combustible; Nov. 5, 2001.
MonoGas, Sensor Devices; Mar. 1998.
International Environmental Technology, May/Jun. 2006 issue, vol. 16, Issue 3, Carbon Dioxide Measures up as a Real Hazard, by Robert E. Henderson.

* cited by examiner

*Primary Examiner*—David Porta
*Assistant Examiner*—Djura Malevic
(74) *Attorney, Agent, or Firm*—Ryan Kromholz & Manion, S.C.

(57) ABSTRACT

A gas sensor of the type that detects the presence of a specific gas by monitoring the absorption of optical radiation transmitted through a chamber containing a sample of gas under test comprises an optical source for emitting radiation therefrom and a detector sensitive to radiation emitted from the source at opposing ends of a circumferential chamber, having optically reflective surfaces, extending around the periphery of a sensor housing. The optical pathway between the source and detector may include a radial portion, a circumferential portion and an axial portion to allow a compact optical path. The gas sensor includes, within a single housing, electronic circuitry for conditioning the electrical output of the detector to provide an output that is a function of at least one selected gas concentration and which is automatically compensated for at least one of temperature, pressure, humidity, and range normalization.

28 Claims, 6 Drawing Sheets

GAS SENSOR

RELATED APPLICATIONS

This application claims the benefit, under 35 U.S.C. §119, of GB 0328684.6, filed Dec. 9, 2003, and GB 0414127.1, filed Jun. 24, 2004.

FIELD OF THE INVENTION

The present invention relates to gas sensors, and in particular to gas sensing devices that detect the presence of a specific gas by monitoring the absorption of optical radiation transmitted through a chamber containing a sample of gas under test.

BACKGROUND OF THE INVENTION

Gas sensors utilizing an infra-red source and a corresponding infra-red detector are well known, in particular in the design of, for example, carbon dioxide and hydrocarbon gas detectors. Infra-red radiation emitted by the source is focused onto the detector, having passed through a chamber containing the gas under test, where some of the infra-red radiation will be absorbed by the gas. The absorption by a specific gas is a function of the wavelength of the infra-red radiation, and by careful selection of an appropriate optical band-pass filter at the detector, it is possible to determine the presence of a specific gas.

A particularly compact form of optical gas sensor has been described in GB 2372099 B to Dynament Limited, and is shown in FIGS. 1 to 3. A gas sensor 1 comprises an optical source 2 for emitting radiation in the optical spectrum and a detector 3 for detection of radiation emitted by the source 2. The source 2 and detector 3 are respectively located at opposite ends of an optical pathway 4 (FIG. 2) which pathway is defined by a circumferential chamber 5 and a central chamber 6 respectively defining a generally circumferential portion 4a of the optical pathway 4 and a generally radial portion 4b of the optical pathway.

As best seen in FIG. 3, the circumferential chamber 5 is defined by: a chamber base 7; an internal surface of an outer cylindrical wall 8 of the sensor housing; an external surface of an inner cylindrical wall 9 of the sensor housing; and a radial end wall 10. The central chamber 6 is defined by an internal surface of the housing base 11 and an internal surface of the inner cylindrical wall 9 of the sensor housing. The housing base 11 provides a planar reflective surface, in the central chamber 6.

Optical communication between the circumferential chamber 5 and the central chamber 6 is by way of a gap 12 in the inner cylindrical wall 9. To enhance reflection of radiation from the circumferential chamber 5 to the central chamber 6, a deflector element 13 provides a reflecting surface 14 which generally extends from the outer cylindrical wall 8 to the inner cylindrical wall 9.

The top 16 of the sensor housing includes a gas permeable window 17 to allow controlled diffusion of gas under test from the external ambient of the sensor housing to the optical pathway 4 in the chambers 5 and 6. The gas permeable window 17 typically comprises a disc shaped element of sintered flame arresting material that allows diffusion of gas but forms a combustion barrier so that the source 2 cannot accidentally act as an ignition source when the sensor is operating in a hazardous and combustible gaseous environment.

The detector 3 is mounted in the base 11 of the sensor housing and comprises a dual element pyroelectric detector. The detector elements 3a, 3b are arranged in a spaced relationship along a vertical axis V of the sensor housing, i.e. an axis parallel to the central axis defined by the inner and outer cylindrical walls 8, 9. This axial spacing of the detector elements 3a, 3b ensures that the characteristics of the optical pathway leading to each of the elements are substantially similar. Each element 3a, 3b includes a filter (not shown) to allow the transmission of optical radiation at selected frequencies or frequency ranges. This dual element configuration enables the sensor to operate with one reference or compensation detector to increase accuracy of the measurements, as will be described hereinafter.

In use, the incandescent source 2 emits infra-red radiation over a broad spectrum of frequencies. The reflective surfaces formed by the inner and outer cylindrical walls 8, 9 and the radial end wall 10 guide the infra-red radiation around the circumferential chamber 5. The non-focussing nature of the reflector surfaces means that positioning of the source 2 within the circumferential chamber 5 is not critical. Once the radiation reaches the other end of the circumferential chamber 5, via optical pathway 4a, radiation is reflected off the reflecting surface 14 of deflector 13 onto the radial inward optical path 4b, towards the detector elements 3a, 3b.

A potential disadvantage with optical gas sensors, as opposed to other types of gas sensor, is that the detector output is not directly related to gas concentration. Therefore, complex signal processing must ordinarily be performed on the detector output in order for it to provide a reliable and accurate signal indicating the gas concentration.

In conventional gas detection equipment, this complex signal processing is generally carried out by electronics that is external to the sensor housing. The reason for this is typically an issue of space. It is desirable to adhere to industry standard dimensions in the construction of sensor housings to ensure backward compatibility with installed gas detection equipment.

Even though some limited signal processing may be carried out within the sensor housing, this is generally limited to relatively simple and straightforward functions such as zero adjustment, rectification and filtering to remove noise from the output. These functions do not require extensive signal processing capacity. Typically, these functions are carried out in the analogue domain. More complex processing such as the derivation of the gas concentration and linearization of the output signal taking into account temperature compensation, pressure compensation and other functions have hitherto been performed remote from the sensor housing.

SUMMARY OF THE INVENTION

It is an object of the present invention to provide a highly compact optical path arrangement for gas sensor.

It is a further object of the present invention to provide an integrated gas sensor which provides both optical gas sensing components as well as signal processing electronics within a single sensor housing.

According to one aspect, the present invention provides a gas sensor comprising:

an optical source for emitting radiation therefrom;

a detector sensitive to radiation emitted from the source;

an optical pathway extending between the source and the detector;

a chamber having optically reflective surfaces defining a substantially circular portion of the optical pathway, a substantially radial portion of the optical pathway, and a substantially axial portion of the optical pathway;

at least a first reflector oriented generally at an oblique angle to the circular portion to separate the circular portion and the radial portion, and at least a second reflector oriented generally at an oblique angle to the plane of the circular portion of the optical pathway to separate the radial portion from the axial portion.

According to another aspect, the present invention provides an integrated gas sensor comprising, within a single housing:

an optical source for emitting radiation therefrom;

a detector sensitive to radiation emitted from the source;

an optical pathway extending between the source and the detector; and electronic circuitry for conditioning the electrical output of the detector to provide a sensor output that is a function of at least one selected gas concentration and which is automatically compensated for at least one of temperature, pressure, humidity, and range normalization.

According to another aspect, the present invention provides an integrated gas sensor comprising, within a single housing:

an optical source for emitting radiation therefrom;

a detector sensitive to radiation emitted from the source;

an optical pathway extending between the source and the detector; and electronic circuitry for conditioning the electrical output of the detector to provide a sensor output signal that has been mathematically processed to take into account at least one of temperature, pressure, humidity and range normalization, and that is directly proportional to at least one selected gas concentration.

DESCRIPTION OF THE DRAWINGS

Embodiments of the present invention will now be described by way of example and with reference to the accompanying drawings in which.

DESCRIPTION OF THE INVENTION

Figure 1:
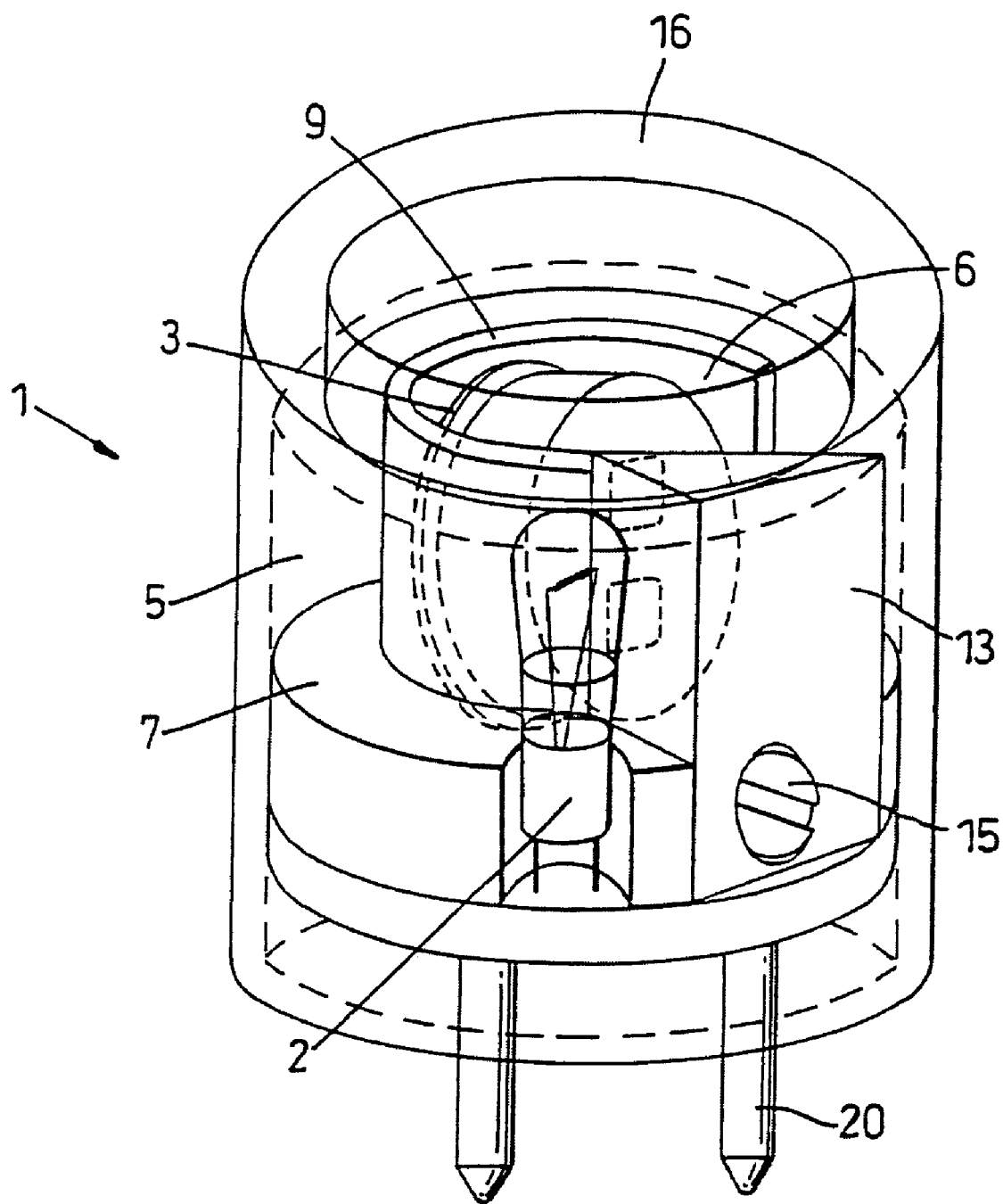
FIG. 1 is a schematic perspective view of a prior art optical gas sensor showing internal detail.
Figure 2:
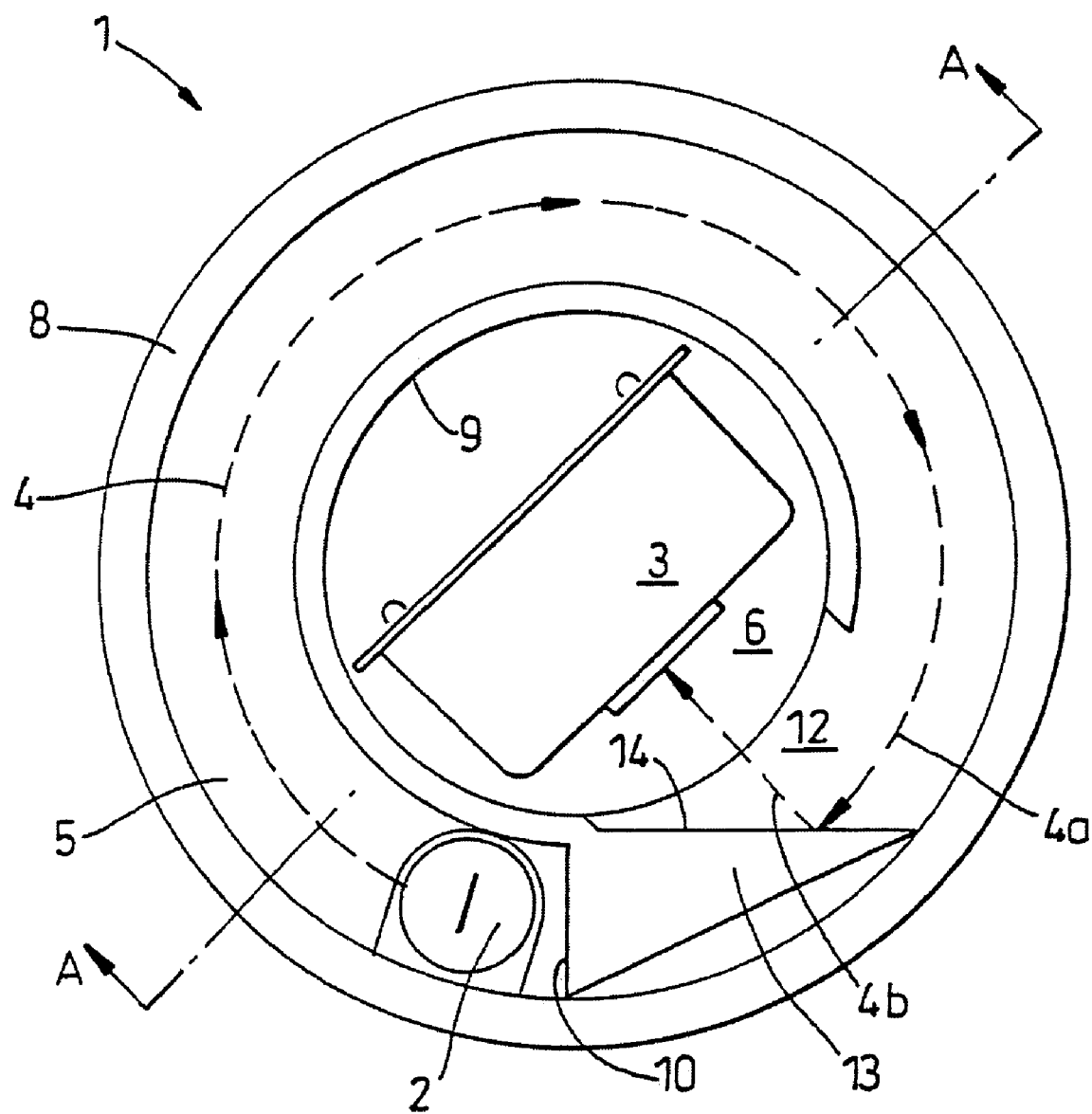
FIG. 2 is a plan view of the sensor of FIG. 1, with the top cover removed.
Figure 3:
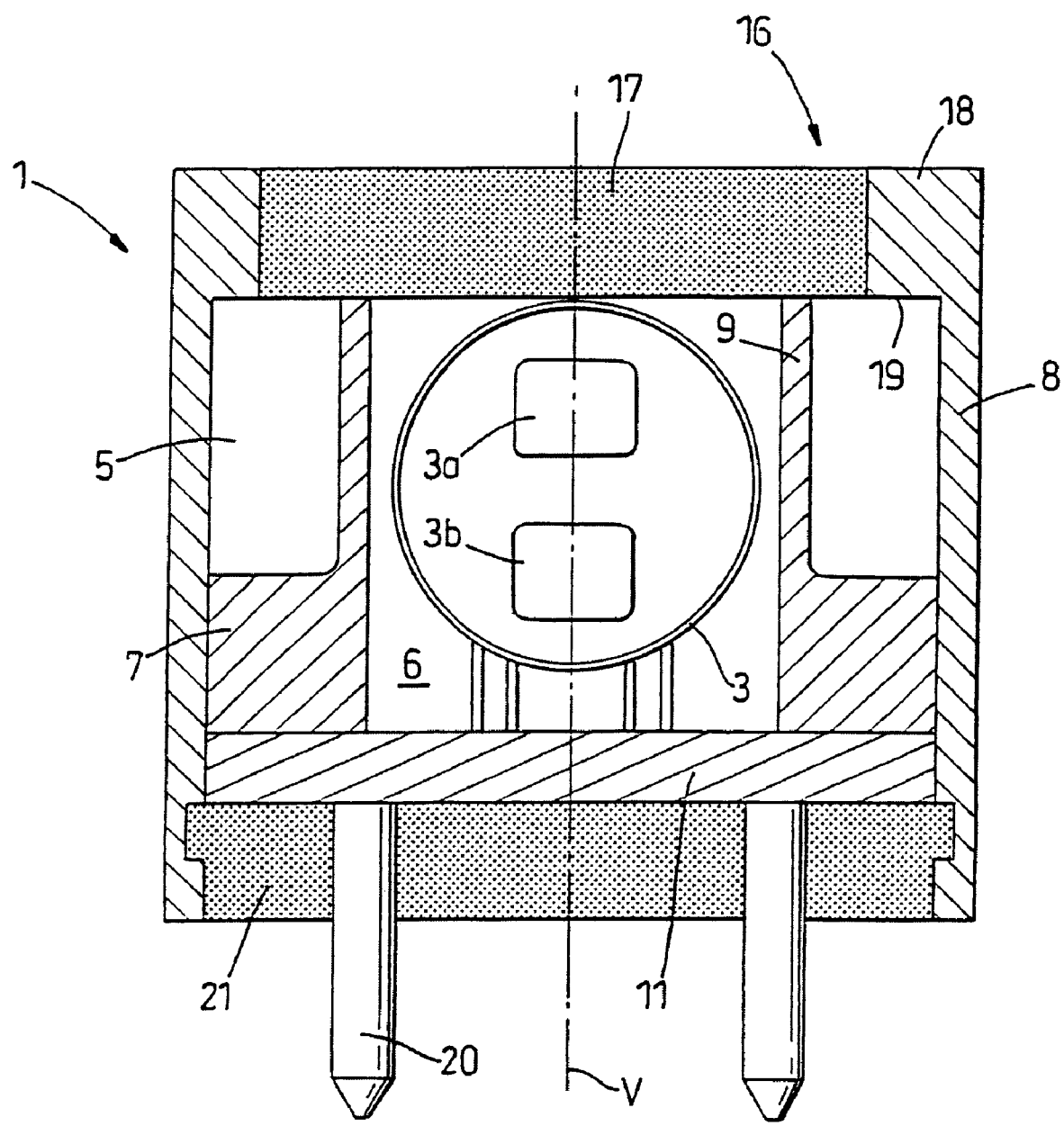
FIG. 3 is a cross-sectional side view taken on line A—A.

The optical gas sensor of FIGS. 1 to 3 has been described in detail above. As will now be described in connection with FIGS. 4 to 7, a significant modification to the layout of the optical components of FIGS. 1 to 3 has been made which substantially decreases the headroom required for these optical components. This, in turn, allows for a substantial increase in the space available for electronic components, so as to enable the inclusion of signal processing circuitry, for a given sensor housing size. Alternatively, if no additional electronic components are required other than those already provided within the sensor housing of FIG. 1, then the arrangement of FIGS. 4 to 7 allows construction of a very low profile sensor housing.

Throughout the present specification, expressions of relative position such as "top", "bottom", "cap", "base", "up", "down" etc, are used solely for convenience and clarity in relation to the sensor as oriented in the drawings. They are in no way intended to be limiting as to the orientation of use of the sensors described.

With reference to FIGS. 4 to 7, a gas sensor 41 comprises a non-focused optical source 42 for emitting radiation in the optical spectrum. The expression "optical" is intended to cover all parts of the electromagnetic spectrum that are useful for the function of gas detection by absorption and includes the infra-red, visible, and ultra-violet ranges of the electromagnetic spectrum. The source 42 is preferably of the incandescent variety, producing a broad range of frequencies with which to measure absorption characteristics, but may also be of the solid state variety such as diodes producing limited frequencies or frequency bands.

The gas sensor 41 further comprises a detector 43 for detection of radiation emitted by the source 42. The detector 43 may be of any suitable type for sensing variations in intensity of radiation received from the source and providing as output a voltage or current as a function thereof. In a preferred embodiment, operating in the infra-red spectrum, the detector 43 is a pyroelectric detector.

The source 42 and detector 43 are respectively located at opposite ends of an optical pathway 44 (FIGS. 5 and 6) which pathway is defined by a circumferential chamber 45 and a central chamber 46 respectively defining a generally circumferential portion 44a of the optical pathway 44 and a generally radial portion 44b of the optical pathway.

The circumferential chamber 45 is defined by: a chamber base 47; an internal surface of an outer cylindrical wall 48 of the sensor housing; an external surface of an inner cylindrical wall 49 of the sensor housing; and a radial end wall 50. Preferably, the chamber base 47 provides a planar reflective surface. Preferably, the chamber base 47 provides a gas-tight fit against the sensor housing outer cylindrical wall 48 by way of an o-ring seal 74.

Although in the preferred embodiment the walls of the circumferential chamber 45 are formed from cylindrical walls 48, 49, it will be understood that some departure from smooth convex and concave surfaces is possible, for example using a multifaceted configuration to form generally circumferential walls. The circumferential walls 48, 49 could also be concave or convex along the axial direction. The radial end wall 50 is preferably planar.

The central chamber 46 is defined by an internal surface of the housing base 51 and an internal surface of the inner cylindrical wall 49 of the sensor housing. The housing base 51 provides a planar reflective surface, in the central chamber 46. Although, in the preferred embodiment, the curved wall of the central chamber 46 is formed from the inner cylindrical wall 49, it will be understood that some departure from a smooth concave surface is possible, for example using a multifaceted configuration to form the internal surface. The internal surface of the inner cylindrical wall 49 could also be concave or convex along the axial direction.

Optical communication between the circumferential chamber 45 and the central chamber 46 is by way of a gap 52 in the inner cylindrical wall 49. To enhance reflection of radiation from the circumferential chamber 45 to the central chamber 46, a deflector element 53 provides a reflecting surface 54 which generally extends from the outer cylindrical wall 48 to the inner cylindrical wall 49. The reflecting surface 54 is preferably planar. The reflecting surface 54 is generally oblique to the tangent of the outer and inner circumferential walls 48, 49 at the position of the gap 52, but may also be radial.

The deflector 53 is preferably formed from a wedge shaped element which also forms the radial end wall 50. The wedge shaped element may also be oblique (rather than orthogonal) to the chamber base 47 so that light from the circumferential optical path 44a is directed at least partially upwards. Alternatively, the deflector 53 on the wedge shaped element may be comprised of multiple facets each at an oblique angle to the chamber base 47 so that light from the circumferential optical path 44a is directed at least partially upwards.

The top 56 of the sensor housing includes a gas permeable window 57 to allow controlled diffusion of gas under test from the external ambient of the sensor housing to the optical pathway 44 in the chambers 45 and 46. Preferably, the gas permeable window 57 comprises a disc shaped element of wire mesh forming a flame arrester. The flame arrester could alternatively use any flame arresting material that allows diffusion of gas but forms a combustion barrier so that the source 42 cannot accidentally act as an ignition source when the sensor is operating in a hazardous and combustible gaseous environment.

Preferably, the disc element 57 has a radius that is greater than the radius of the inner cylindrical wall 49 and less than the radius of the outer cylindrical wall 48 so that the gas permeable window completely extends over the central chamber 46 and partially extends over the circumferential chamber 45. The remaining portion 58 of the top 56 of the sensor housing provides a reflective inner surface 59 partially covering the circumferential chamber 45 to enhance the optical transmission characteristics of the circumferential chamber.

The detector 43 is mounted to the base 51 in the sensor housing and preferably comprises a dual element pyroelectric detector. The detector elements 43a, 43b are preferably arranged in a spaced relationship along a horizontal axis H of the sensor housing, i.e. a diametric axis orthogonal to the central axis defined by the inner and outer cylindrical walls 48, 49. This axial spacing of the detector elements 43a, 43b ensures that the characteristics of the optical pathways leading to each of the elements are substantially similar. Each element 43a, 43b includes a filter (not shown) to allow the transmission of optical radiation at selected frequencies or frequency ranges. This dual element configuration enables the sensor to operate with one reference or compensation detector to increase accuracy of the measurements, as in known in the art.

Electrical leads 60 to both the source 42 and the detector 43 pass through the housing base 51 and through an encapsulant layer 61 that holds the base 51 in position. The encapsulant layer 61 also seals the housing so that it is gas tight except for the controlled diffusion window 57. The encapsulant may be protected by way of a closing plate 62.

Figure 4:
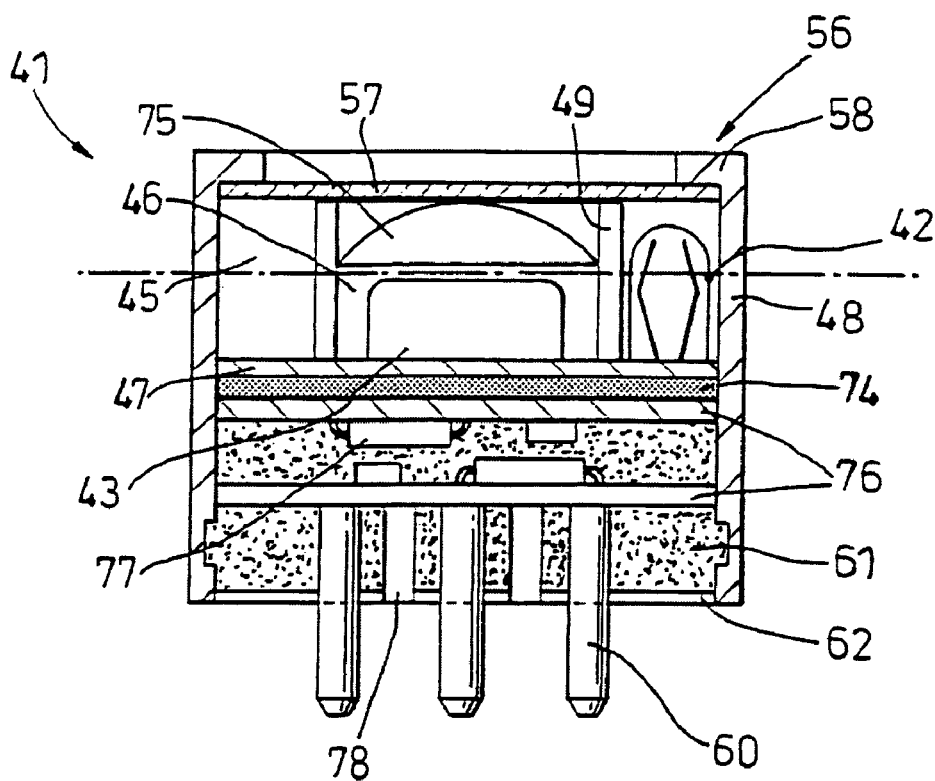
FIG. 4 is a cross-sectional side view of a modified optical gas sensor having substantially reduced headroom for the optical components, according to one embodiment of the present invention.
Figure 6:
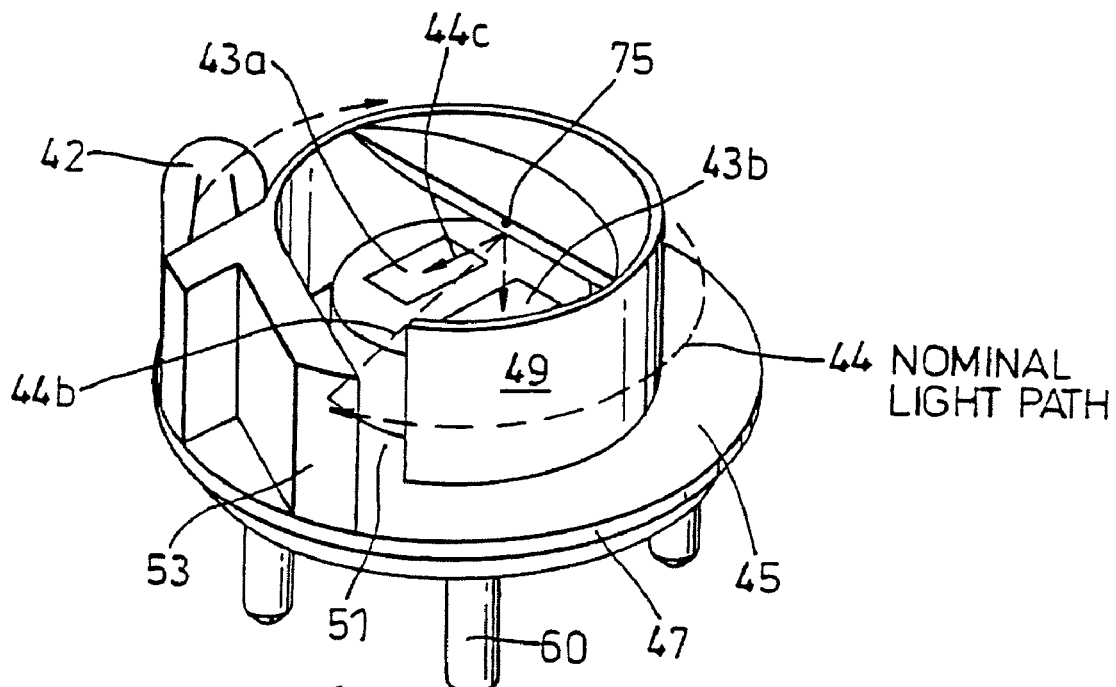
FIG. 6 is a perspective side and top view of the sensor of FIG. 4, with the top and side walls of the sensor housing removed.
Figure 5:
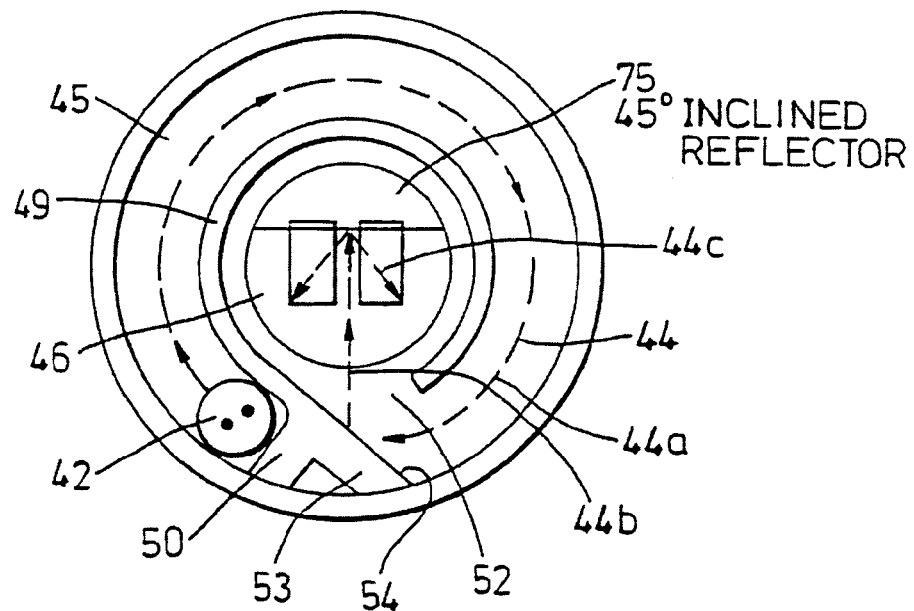
FIG. 5 is a plan view of the sensor of FIG. 4, with the top cover removed.
Figure 7:
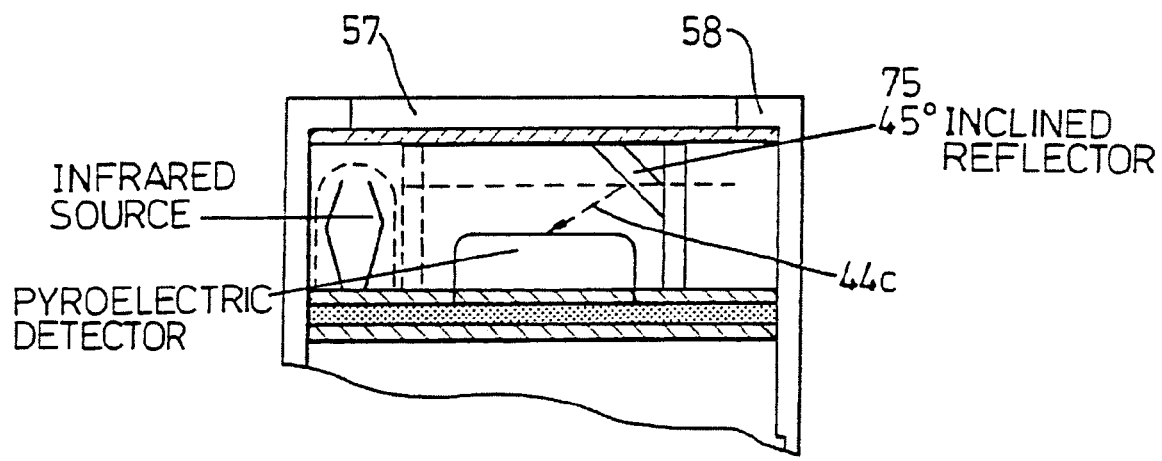
FIG. 7 is a partial cross-sectional side view of the sensor of FIG. 4, on a section that is orthogonal to the section of FIG. 4.

The housing of sensor 41 may be made to conform to an industry standard configuration in terms of external dimensions and positioning of a plurality of electrical leads 60, not all of which are shown in the drawings. Preferably, the overall outside casing diameter is approximately 2 cm, and the casing height is approximately 2 cm. Preferably, the diffusion window 57 and encapsulant layer 61 each have a thickness suitable to meet any applicable safety requirements or regulations. More preferably, the overall outside casing diameter is 20 mm±0.15 mm and the casing height is 16.6 mm±0.15 mm (excluding projecting leads), as shown in FIG. 4, so as to provide backward compatibility with prior art sensor casing styles.

A particular feature of the sensor 41 is that the detector 43 is mounted with its detector elements 43a, 43b disposed on the horizontal axis H, and preferably facing upwards. An inclined reflector 75 is provided with its reflective surface at an oblique angle to the horizontal axis H and facing the gap 52 so that light from the circumferential path 44a and deflector 53 is directed downwards onto the detector elements 43a, 43b along an at least partially axial optical path 44c. Preferably, the inclined reflector presents its reflective surface at an angle of 45 degrees to the horizontal axis H.

In use of the preferred embodiment, the incandescent source 42 emits infra-red radiation over a broad spectrum of frequencies. The reflective surfaces formed by the inner and outer cylindrical walls 48, 49 and the radial end wall 50 guide the infra-red radiation around the circumferential chamber 45. The non-focussing nature of the reflector surfaces means that positioning of the source 42 within the circumferential chamber 45 is not critical. Once the radiation reaches the other end of the circumferential chamber 45, via optical pathway 44a, radiation is reflected off the reflecting surface 54 of deflector 53 onto a primarily radially inward (and possibly slightly axially upward) optical path 44b, towards the inclined reflector 75. From the inclined reflector 75, the radiation is reflected in an axially downward optical path 44c towards the detector elements 43a, 43b. Depending upon the precise configuration1 the optical path 44c may also include a radially inward component.

The preferred planar geometry of the reflecting surface 54 and reflector 75 is such that the radiation incident upon the detector elements 43a, 43b is principally normal to the elements' surfaces which provides optimum temperature characteristics for the sensor 41 and ensures that a substantially equal amount of radiation falls on both elements 43a, 43b. This provides for better matching conditions between the two detector element outputs.

The circumferential optical path 44a also utilizes the space within the sensor housing in a highly efficient manner, and allows the chamber walls 48, 49 to be formed from cylindrical elements that are easy to manufacture and also easy to assemble. The completion of the optical path 44 with the radial portion 44b and axial portion 44c enables the detector to be mounted centrally and with its electrical contact pins directed straight into a printed circuit board 76 with its major dimension lying flat to the printed circuit board. The arrangement also facilitates easy positioning of the detector within the central chamber 46.

As indicated above, the layout of the optical components releases a significant proportion of the sensor housing for signal processing electronics. Below the chamber base 47 and sealed within the encapsulant 61 is the printed circuit board 76 which includes various electronic components 77.

Figure 8:
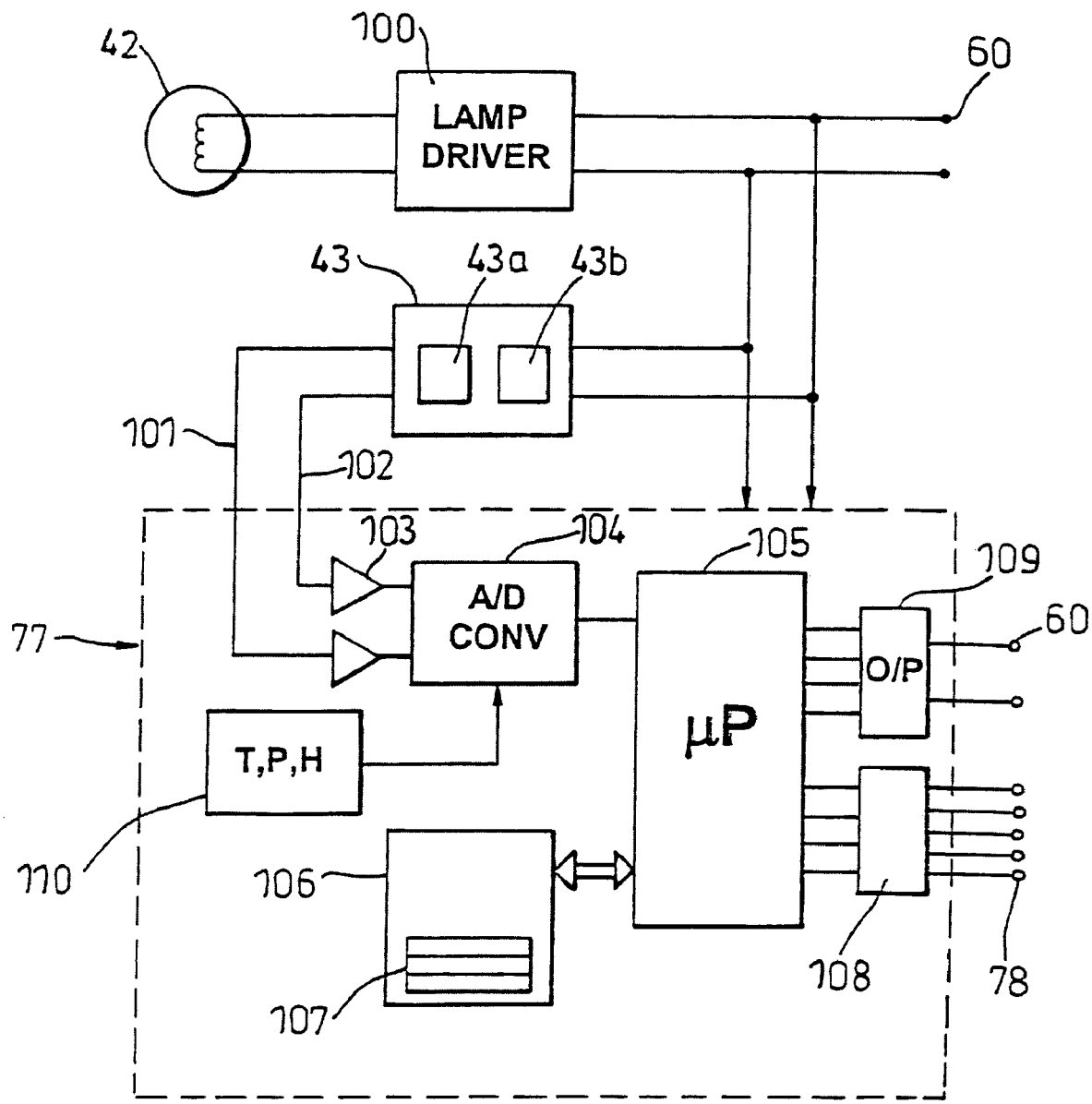
FIG. 8 is a schematic diagram of internal components of the optical gas sensor of FIG. 4.

With reference to FIG. 8, in a preferred embodiment, these electronic components 77 include a driver circuit 100 for the optical source 42. The detector 43 provides two electrical outputs 101, 102 corresponding respectively to the first detector element 43a and the second detector element 43b. The first detector element provides a first output signal on line 101 associated with the absorption spectra of the selected gas for detection, e.g. carbon monoxide. The second detector element provides a second output signal on line 102 associated with a broader spread of frequencies, or preferably a selected bandwidth different from that of the first filter and relatively immune from undesirable attenuation from other common gases, to provide a reference signal. The reference signal is used to provide compensation of the attenuation measured by the first sensor that arises from temperature, humidity, degradation of the source intensity and other obscuration factors, rather than from the presence of the selected gas in the optical pathway 44. The ratio of the reference and selected gas signals will therefore be substantially unaffected by these other factors.

The two output signal lines 101, 102 are connected to a pre-amplification circuit 103, the output from which is connected to an analogue-to-digital converter 104 (hereinafter 'ADC'). The digitised output of the ADC 104 is supplied to a microprocessor 105. The microprocessor 105 is provided with a memory module 106 that is used for program storage and for storing look-up tables 107 (hereinafter 'LUT's') required for computing a gas concentration value from the inputs to the microprocessor. The microprocessor 105 is also preferably provided with an external programming interface 108 which may be implemented by way of programming contacts 78 as shown in FIG. 4. The microprocessor also includes an output path or driver 109 coupled to the electrical leads 60. Where an analogue output is required (e.g. a voltage that is a function of gas concentration), the output driver 109 includes a digital-to-analogue converter (hereinafter 'DAC') for converting the digital output of the microprocessor 105 to a proportional analogue voltage. Where a digital output is required, the output driver 109 may simply comprise an electrical bus.

For ensuring a fully compensated gas concentration output, the gas sensor 41 is preferably also provided with one or more of suitable temperature, pressure and humidity sensors 110 so that any necessary corrections to the detector 43 readings can be made. For sensors that provide an analogue output, the ADC 104, or a further ADC, provide digitized readings to the microprocessor 105.

In a preferred arrangement, the microprocessor 105 uses the LUT's in order to determine corrections for temperature, pressure and/or humidity, according to the accuracy and application required of the specific gas sensor. Alternatively, these corrections could be made by computation according to appropriate formulae, e.g. stored in the microprocessor memory 106. In an alternative configuration, analogue outputs from the temperature, pressure and/or humidity sensors could be used directly to compensate the detector output signals in the analogue domain.

The various components described in connection with FIG. 8 are preferably connected to a common power supply (e.g. 5V DC) by way of the external electrical leads 60. The output driver 109 is similarly connected to the external electrical leads 60.

All of the above components are preferably provided within the sensor 41 housing to result in a fully integrated gas sensor that provides a direct, compensated gas concentration output that requires no further signal processing. Preferably the compensated output is temperature compensated. Preferably, the compensated output is pressure compensated. Preferably the compensated output is humidity compensated.

Preferably, the microprocessor 105 is also configured to calibrate the sensor output so that the sensor output lies within predetermined maximum and minimum end values. This is referred to herein as 'normalization' of the output. Such normalization may be useful to offset any gradual degradation in the optical source performance over time.

Preferably, the microprocessor 105 is also configured to determine the gas concentration versus voltage output slope to ensure that the gas sensor 41 has a desired output characteristic. This is referred to herein as the 'transfer characteristic'. This is particularly useful where it is desired to use the gas sensors as replacement units for other existing types of gas sensor.

For example, pellistor-type gas sensors have particular output characteristics and it may be useful to configure the optical gas sensor 41 such that the output characteristic behaves exactly the same as a pellistor output.

In a preferred arrangement, the programming contacts 78 may be used to configure the output characteristics of the sensor 41. For example, the same optical sensor 41 may be used in a variety of different applications, as a direct replacement for different types of gas sensor (e.g. non-optical), by first switching the characteristics of the sensor 41 using the programming contacts 60. This configuration operation may comprise up-loading predetermined LUT's 107, or selecting an installed LUT for use. The configuration operation may be a one-off event, at the point of manufacture, or may be provided as a user function to be done once on installation, or multiple times during operation of the sensor.

The configuration operation need not be restricted to programming LUT's. For example, variables may be altered for use in formulae used to calculate gas concentrations, and programs or sub-routines may be updated.

In use, the gas permeable window 57 ensures that any changes in gas concentrations external to the sensor housing are rapidly communicated to the optical pathway 44 particularly in the circumferential chamber 45, to be sensed by the detector elements 43a, 43b, providing good real time output of sensed gas conditions. The preferred design of gas permeable window 57 as shown ensures that natural diffusion of gas into the circumferential chamber 45 is sufficient so that no pumping of gas through the chamber is required. In addition, having temperature, pressure and/or humidity sensor located within the housing very close to, or within, the optical chamber housing, ensures that changes in environmental conditions are rapidly communicated to the sensor output.

A number of variations to the embodiments described above are possible.

For example, although the preferred embodiment provides the source 42 located at the closed end of the circumferential chamber 45, and the detector 43 located in the central chamber 46, it will be understood that these positions may be reversed.

The illustrated embodiment shows a gas sensor 41 having an optical path which includes the circumferential portion 44a, the radial portion 44b and an axial downward portion 44c. However, it will be understood that the detector could be inverted and positioned adjacent to the top 56 of the sensor in which case an axial upward portion of the optical pathway would be required. This arrangement would be less preferred as the coupling of the detector 43 to the associated electronic components 77 would be more complex and at least part of the gas permeable window 57 may be occluded.

The circumferential chamber 45 need not be exactly circular to provide a substantially circular portion of the optical pathway. For example, a polygonal package, e.g. hexagonal, could include a circumferential chamber extending around the sides of the hexagon. The circumferential chamber may also be of a spiral configuration, in which the chamber wraps over itself after one complete circuit of the periphery of the chamber.

In all of the above described embodiments, some or all of the reflective surfaces may be gold coated (or coated with other suitable reflective material) to enhance signal amplitude, and/or coated with a passivation layer to provide protection against corrosive gases.

The gas permeable window 57 could also be formed from other materials, such as a gauze screen. The gas permeable window 57 need not be disc shaped, but could comprise a series of discrete openings in the top of the housing or be annular in shape.

The detector 43 need not be of the dual element type if a reference detector is not required. Multiple detector elements, each with an appropriate filter, may be provided for simultaneous detection of more than one selected gas.

Other embodiments are intentionally within the scope of the accompanying claims.

The invention claimed is:

1. A gas sensor comprising
an optical source for emitting radiation therefrom,
a detector sensitive to radiation emitted from the source,
an optical pathway extending between the source and the detector,
a chamber having optically reflective surfaces defining a substantially circular portion of the optical pathway, a substantially radial portion of the optical pathway, and a substantially axial portion of the optical pathway,
at least a first reflector oriented generally at an oblique angle to the circular portion to separate the circular portion and the radial portion, and
at least a second reflector oriented generally at an oblique angle to the plane of the circular portion of the optical pathway to separate the radial portion from the axial portion.

2. The gas sensor of claim 1
wherein the chamber is defined by outer and inner circumferential walls of a substantially cylindrical housing, the circular portion of the optical pathway lying between the outer and inner circumferential walls and the radial and axial portions of the optical pathway lying within the inner circumferential walls.

3. The gas sensor of claim 2
wherein the first reflector comprises an end wall extending generally radially between the outer and inner circumferential walls and at an oblique angle to a tangent of the outer or inner circumferential walls, to reflect light through a gap in the inner circumferential wall into a central chamber and to the substantially radial portion of the optical pathway.

4. The gas sensor of claim 2
wherein the source is located at an end of the circular portion of the optical pathway distal from the first reflector.

5. The gas sensor of claim 4
wherein the detector is located within the central chamber with its detection surface substantially orthogonal to the axial portion of the optical pathway.

6. The gas sensor of claim 2, further comprising
a chamber cover forming a closure for the cylindrical housing, the chamber cover including a reflective inner surface in combination with a gas permeable member.

7. The gas sensor of claim 6
wherein the gas permeable member comprises a flame arresting material.

8. The gas sensor of claim 6
wherein the gas permeable member covers an annular portion of the circumferential chamber.

9. The gas sensor of claim 8
wherein the gas permeable member comprises a disc of radius greater than said inner circumferential wall and less than said outer circumferential wall.

10. The gas sensor of claim 5
wherein the detection surface comprises two detector elements spaced apart along an axis substantially diametric to the circumferential walls and orthogonal to the axis of the inner and outer circumferential walls.

11. The gas sensor of claim 1
wherein the sensor is contained within a single housing, and further including
electronic components therein for processing signals from the detector to generate a predetermined output characteristic.

12. The gas sensor of claim 11
wherein the electronic components include means for generating a compensated output from the sensor as a function of gas concentration.

13. The gas sensor of claim 12
wherein the compensated output is any one or more of temperature-compensated, pressure-compensated and humidity-compensated.

14. The gas sensor of claim 11
wherein the electronic components include means for generating a normalized output from the sensor as a function of gas concentration.

15. The gas sensor of claim 14
wherein the normalized output has predetermined maximum and minimum end points.

16. The gas sensor of claim 1, further including
a programming interface for externally presetting the output characteristics of the sensor.

17. The gas sensor of claim 1
wherein the housing dimensions include an overall outside housing diameter of approximately 2 cm, and a housing height of approximately 2 cm.

18. The gas sensor of claim 1
wherein the housing dimensions include an overall outside housing diameter of 20 mm±0.15 mm and a housing height of 16.6 mm±0.15 mm.

19. An integrated gas sensor comprising
a housing having dimensions comprising an overall outside housing diameter of 20 mm±0.15 mm and a housing height of 16.6 mm±0.15 mm,
an optical pathway carried by the housing for containing at least one selected gas concentration,
an optical source carried by the housing in communication with the optical pathway for emitting radiation into the optical pathway,
a detector that is carried by the housing in communication with the optical pathway and that is sensitive to radiation emitted from the optical source for providing an electrical output that varies as a function of variations of radiation intensity in the optical pathway, and
electronic circuitry carried by the housing coupled to the detector for receiving the electrical output, the electronic circuitry including pellistor-type gas sensor emulation means for conditioning the electrical output of the detector to provide a sensor output that is a linear function of the at least one selected gas concentration and that is automatically compensated for at least one of temperature, pressure, humidity, and range normalization for outputting the sensor output directly to a pellistor-type gas detector.

20. The gas sensor of claim 19, further including
a temperature sensor for sensing a prevailing temperature, and
wherein the pellistor-type gas sensor emulation means compensates the electrical output according to the prevailing temperature.

21. The gas sensor of claim 19, further including
a humidity sensor for sensing a prevailing humidity, and
wherein the pellistor-type gas sensor emulation means compensates the electrical output according to the prevailing humidity.

22. The gas sensor of claim 19, further including
a pressure sensor for sensing a prevailing pressure, and
wherein the pellistor-type gas sensor emulation means compensates the electrical output according to the prevailing pressure.

23. The gas sensor of claim 19,
wherein the pellistor-type gas sensor emulation means includes a normalization circuit for compensating the electrical output to lie within a predetermined voltage range.

24. The gas sensor of claim 19,
wherein the pellistor-type gas sensor emulation means includes a microprocessor.

25. The gas sensor of claim 24, further including
a look-up table for applying compensation values to the sensor output.

26. The gas sensor of claim 24, further including
a programming interface for selecting one of a plurality of possible output characteristics of the sensor.

27. The gas sensor of claim 26
wherein the programming interface may be used to upload a plurality of data values to determine the output characteristics of the sensor.

28. The gas sensor of claim 19
wherein the housing dimensions include an overall outside housing diameter of approximately 2 cm, and a housing height of approximately 2 cm.

* * * * *